United States Patent [19]
Dykmans

[11] 4,302,979
[45] Dec. 1, 1981

[54] MEANS AND TECHNIQUES USEFUL IN STRESSING CABLE

[76] Inventor: Maximiliaan J. Dykmans, Box 696, El Cajon, Calif. 92022

[21] Appl. No.: 883,936

[22] Filed: Mar. 6, 1978

Related U.S. Application Data

[63] Continuation of Ser. No. 678,890, Apr. 21, 1976, abandoned, which is a continuation of Ser. No. 519,938, Nov. 1, 1974, abandoned, which is a continuation of Ser. No. 323,760, Jan. 15, 1973, abandoned, which is a continuation-in-part of Ser. No. 153,601, Jun. 16, 1971, abandoned.

[51] Int. Cl.³ .......................... G01N 3/36; B28B 21/60
[52] U.S. Cl. .................................... 73/828; 254/29 A
[58] Field of Search ............... 73/95.5, 95, 89, 88 R, 73/828, 826; 254/29 A

[56] References Cited

U.S. PATENT DOCUMENTS

| | | | |
|---|---|---|---|
| 2,651,196 | 9/1953 | Pinkel | 73/95.5 |
| 2,711,291 | 6/1955 | Kennedy | 242/7.22 |
| 2,721,109 | 10/1955 | Ross | 346/29 |
| 2,889,706 | 6/1959 | Huyser | 73/89 |
| 3,057,190 | 10/1962 | Minke | 73/89 |
| 3,090,598 | 5/1963 | Paul | 254/29 A |
| 3,138,952 | 6/1964 | Dobbins | 73/89 |
| 3,354,705 | 11/1967 | Dyer | 73/95 |
| 3,543,569 | 12/1970 | Carter | 73/95 |
| 3,588,045 | 6/1971 | Stubbs | 254/29 A |

FOREIGN PATENT DOCUMENTS

1796418  7/1959  Fed. Rep. of Germany.
36-4697  5/1961  Japan.

Primary Examiner—Stephen A. Kreitman
Attorney, Agent, or Firm—Lyon & Lyon

[57] ABSTRACT

A permanent recording is made of the force applied to a prestressing element such as a steel cable as well as its resulting elongation in the process of taking up its slack and in subsequently tensioning and locking off the cable in its final stressed condition, such recording being particularly useful in establishing actual values of stress and strain along a cable length inside of a tube which is in frictional engagement with the cable.

21 Claims, 12 Drawing Figures

FIG. 10. RECORDED ELONGATION

RECORDED ELONGATION

RECORDED ELONGATION

MEANS AND TECHNIQUES USEFUL IN STRESSING CABLE

This is a continuation of application Ser. No. 678,890, filed April 21, 1976 which is a continuation of my U.S. Application Ser. No. 519,938, filed Nov. 1, 1974 which is a continuation of my U.S. Application Ser. No. 323,760, filed Jan. 15, 1973 which in turn is a continuation in part of my Application Ser. No. 153,601, filed June 16, 1971 now all abandoned.

The present invention relates to improved means and techniques useful in pretensioning and also in posttensioning operations and serves to provide a useful, permanent record of conditions existing along a long length of cable inside a tube at the time of applying forces to the prestressing element such as, for example, a steel cable.

An object of the present invention is to provide permanently recorded information as to both the force applied to a prestressing element and its resulting elongation.

Another object of the present invention is to provide a recording of the presence of an effect of such factors as friction, binding, changes in modulus of elasticity, wedge seating losses, and breakaway forces required to release wedges from their cable locking position.

Another object of the present invention is to provide means and techniques whereby the actual stresses in a cable along its entire length may be accurately ascertained during its stressing when, for example, such cable is in frictional engagement with a tubular conduit.

Another object of the present invention is to provide means and techniques whereby long lengths of cable may be safely stressed with an indication of abnormal conditions and safety features being brought into play when the cable is of substandard quality.

The features of the present invention which are believed to be novel are set forth with particularity in the appended claims. This invention itself, both as to its organization and manner of operation, together with further objects and advantages thereof, may be best understood by reference to the following description taken in connection with the accompanying drawings in which:

Figure 1:
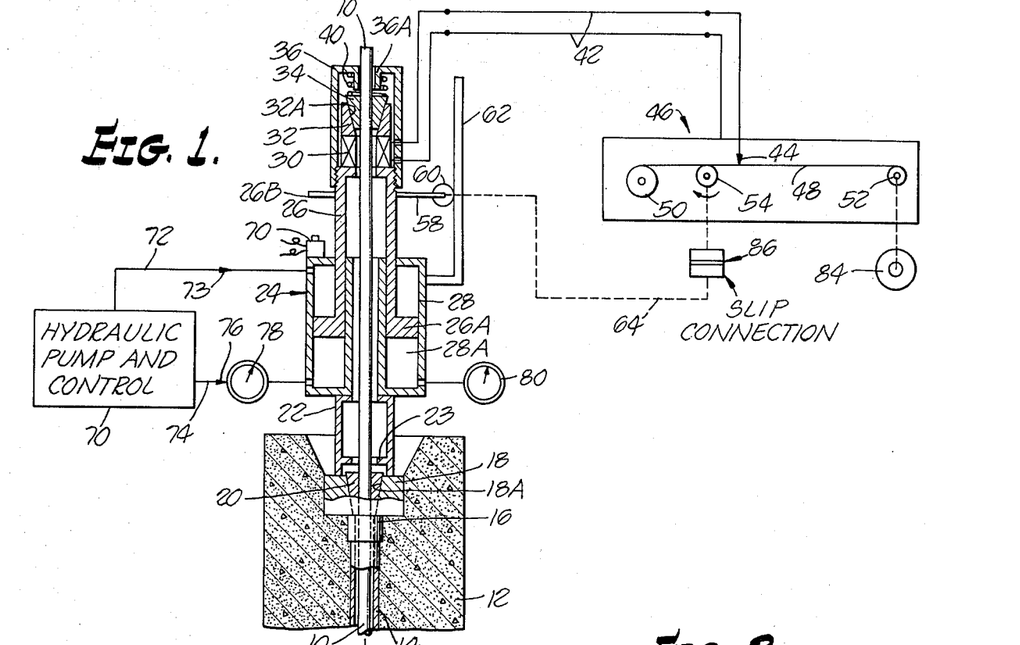
FIG. 1 illustrates a system embodying features of the present invention.

In FIG. 1 the prestressing cable 10 may be part of many different structures in which prestressing is desired, such as, for example, in bridges, tanks, pipes, buildings, and pilings where the prestressing cable may or may not be associated with concrete.

As illustrated for examplary purposes, the cable 10 is used in prestressing concrete 12 through which the cable 10 extends. One end of the cable 10 is stationarily anchored, as, for example, in the concrete itself by conventional means not illustrated. It will be appreciated that the invention is applicable to not only posttensioning uses which are described in detail herein but also to pretensioning operations wherein a cable is stressed and maintained in a stressed condition while concrete is poured and allowed to harden around the prestressed reinforcing steel. Further, it will be appreciated that the stressing cable may, as illustrated, be of steel but may also be glass rope, asbestos rope, or made of other materials that are suitable for use in prestressing operations.

The cable 10 extends, in turn, upwardly through a tube 14 within the concrete 12, through a coupling 16 and an anchor plate 18 within which are multiple wedge cable gripping elements 20 that engage the cable 10 for locking the cable 10 to the anchor plate 18 in conventional manner. The coupling 16 may be welded to the anchor plate 18 and sealingly connected to the tube 14 as, for example, by taping or by screwthreads.

The anchor plate 18 has a conical opening 18A within which two or more wedge segments 20 are slidably mounted with the inner portions of such wedge segments being serrated or otherwise formed to provide a good frictional or locking engagement with the cable 10.

Mounted on the anchor plate 18 is a jack stand 22 which is used to support a hydraulic ram 24. This jack stand 22 is provided with an inwardly extending flange portion 23 which is under certain conditions engageable with the wedge grip segments 20 to cause these segments 20 to become disengaged from the cable 10.

The ram 24 is of conventional construction and incorporates a double acting piston 26 within a stationary cylinder 28, the cylinder 28 and piston 26 having openings through which the cable 10 extends.

A load cell 30 in the nature of a transducer which produces an electrical output in accordance with forces applied thereto is disposed between the upper end of piston 26 and a temporary anchor plate 32 which like the anchor plate 18 has a conical opening 32A within which a plurality of conical wedge gripping segments 34 are slidably mounted for likewise frictionally engaging and locking the cable 10 extending therethrough.

The piston 26 may be provided with a cap member 36 screwthreaded thereon and which serves as a seat for one end of a coil compression spring 40 that has its other end bearing on the wedge segments 34 to urge such segments into frictional engagement with cable 10. Optionally a like spring (not shown) may be positioned between the flange 22 and wedge segments 20 for the same purpose. This cap 36 has downwardly extending flange portion 36A which is engageable with the wedge gripping segments 34 under certain conditions and in general accomplish a functional like that accomplished by the flange portion 23.

The load cell 30 has its electrical output transferred via a pair of wires 42 to the recording element 44 of a graph paper recorder 46 in which paper 48 is transferred from a supply reel 50 to a takeup reel 52 by a paper drive roller 54 which for that purpose has peripheral teeth that in conventional manner engage perforations 49 in paper 48 for driving the same.

This paper drive roller 54 is driven in accordance with movement of the piston 26 which as illustrated has an arm 58 extending therefrom on which a roller 60 is rotatably mounted for rotation on a track member 62 connected to the cylinder 28. This roller 60 drives the paper roll 54 through a connection illustrated by the dotted line 64 so that, for example, for each inch of movement of piston 26 there is one inch of movement of paper 48. It is noted that the paper is driven in a forward direction, i.e. to the right in FIG. 2 when the piston 26 is extended and moves in the opposite direction, i.e. to the left when the piston 26 is retracted.

This extended and retracted movement of piston 26 is accomplished in conventional manner by controlling the direction of fluid flow to the cylinder 28 from the hydralic pump and control 70. Thus when oil under pressure flows in line 72 in the direction indicated by arrow 73, the piston 26 moves downwardly in its retracted direction and conversely, when oil under pressure flows in the line 74 in the direction indicated by arrow 76, the piston 26 is extended. This latter pressure is indicated by pressure gauge 78 in line 74. Also a pressure gauge 80 may be connected to a tapped opening in cylinder 28 below the piston portion to indicate the pressure in the lower end of cylinder 28.

In operation of the system it is assumed that initially there is some slack in the cable 10. This slack is removed and the cable is tensioned by applying hydraulic pressure to the lower cylinder portion 28A (defined in part by piston portion 26A). This causes the piston 26 to move upwardly and thereby cause the anchor block or plate 32 to move upwardly into engagement with wedge grip segments 34 and the serrations thereon cause these segments 34 to grip the cable 10 so that such upward movement of piston 26 also causes the paper 48 to move to the right in FIG. 2.

It is assumed that slack was in the cable, hence initial movement of piston 26 produces substantially no or very little force on the load cell 30 in which case the electrical output of such cell is at a very low minimum value. This value is recorded and appears as a substantially straight line extending between points A and B. This line may under some conditions be other than straight as, for example, when there is frictional contact between the cable and tube 14 or more noticeably when there is some binding action. When present, such such friction and binding results in a characteristic recording which identifies the same as such.

Point B represents the condition where all slack has been removed and the cable is becoming taut or tensioned as a result of further upward movement of piston 26. In such further upward movement the paper 48 moves a commensurate amount to the right and the load cell is increasingly compressed between piston 26 and anchor plate 32 causing increasing electrical output which is recorded as a substantially straight line when the modulus of elasticity of the cable remains constant and also when the friction coefficient between cable 10 and tube 14 remains unchaged. If this is not the case, the recording instead of being a straight line may have some curvature which in itself is revealing of prevailing cable conditons.

The stroke of piston 26 is of predetermined maximum length, and this length may be shorter than the necessary elongation of the cable for the desired ultimate applied prestressing force in which case the stressing is accomplished in successive stages wherein the piston is extended, then retracted, and then extended a number of times depending upon the necessary cable elongation. In its movement to its extended position, as explained previously, the recording is illustrated as being linear, i.e. a straight line between points B and C in FIG. 2. During subsequent retraction of piston 26, the cable 10 with the gripping segments 20 moves downwardly until these segments 20 seat in anchor plate 18 and grip cable 10. This appears as a recording of the line CD in FIG. 2 which represents a decrease in tension and also a decrease in elongation. After this locking occurs the piston 26 retracts further to its extreme retracted position, and this causes a recording of the lines DE and EA. The line DE results because the wire is gripped by segments 20 and downward movement of piston 26 releases compression forces on load cell 30 causing its output to be substantially zero, which is the ordinate of the point E. Further continued retracted movement causes the paper 48 to move backwards thereby causing the recording from point E to point A. The point A is considered to have a zero ordinate and a zero abscissa. At this stage, the paper is advanced automatically or manually to a new starting position having the same zero, zero co-ordinates namely to point F. For manual advancement, the takeup roll 52 may be provided with aknob 84, and the connection 64 may incorporate a slip connection 86 such as a friction coupling which allows the roll 52 to be rotated without rotation of roller 60. For automatic advancement, a limit switch 90 actuable by the piston arm 26B in its extreme lower position may be used to energize a motor 92 is automatically deenergized. For this latter purpose timer 94 incorporates a switch 96 which is connected in shunt with limit switch 90 and which is closed when timer 94 is first energized but open after a predetermined elapsed timer sufficient to cause displacement of the paper a distance corresponding to the distance between points A and F.

Figure 2:
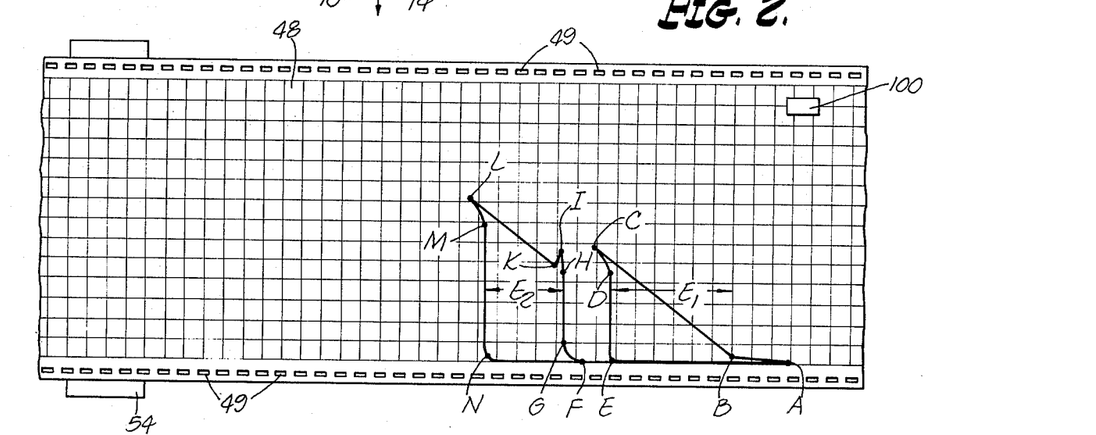
FIG. 2 illustrates one form of recording made in use of the system shown in FIG. 1.

After the paper is thus advanced, pressure is applied to the cylinder chamber 28A to cause the piston 26 to move upwardly; and in its initial movement, wedge segments 34 seat in plate 32, and this initial movement corresponds to curve line FG. After this seating and gripping of cable 10, further upward movement of the piston causes the load cell to be compressed causing its output to increase and thereby cause the recording GH. The ordinate of H which represents force is substantially the same ordinate as point D.

At this stage, the lower wedge segments 20 are in locked condition and additional force is required to break them loose from anchor plate 18, and this is accomplished by applying additional force to the piston 26 causing the load cell 30 to deliver a large output recorded along line HI. After the lower wedge segments break loose, the force on load cell 30 is correspondingly reduced causing the recording to drop from point I to point K. Continued upward movement of the piston causes the load cell to be further compressed causing a recording along the line KL. The force corresponding to point L is in this example higher than the desired lock off force corresponding to the ordinate of point M. At point M the lower wedge segments 20 lock the cable 10 in final stressed condtion. The piston 26 may then be moved to its retracted position causing the recording MNF. The apparatus involving jack stand 22, ram 24, load cell 30 and temporary locking means 32, 34 and cap 36 may then be removed.

The recording thus made allows one to have a permanent record of the force and elongation of the cable 10. The force is the ordinate of point M and the elongation is the sum of distance $E_1$ plus $E_2$ where the distance $E_1$ is the horizontal distance between points D and B and the distance $E_2$ is the horizontal distance between points M and H. Other important information is in that permanent record. For example, the change in modulus of elasticity of the stressing cable is indicated in terms of curvature appearing in lines BC and in lines KL. Also friction and binding if any is also recorded as indicated previously. Also the so-called wedge seating loss appears as the loss in force represented, for example, by the vertical distance between points L and M and the corresponding reduction in elongation measured as the horizontal distance between the same points L and M.

Figure 3:
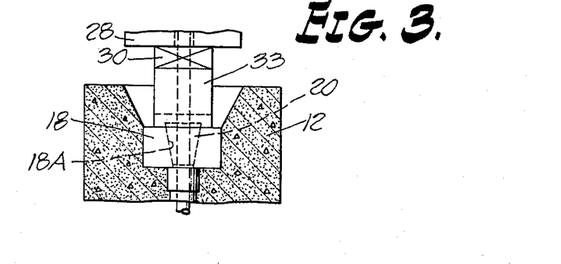
FIG. 3 illustrates an alternate position for the load cell shown in FIG. 1.

Alternatively the load cell 30 instead of being positioned between piston 26 and place 32, may, as illustrated, be positioned between the cylinder 28 and the jack stand 33. Still another modification of the invention resides in rendering the load cell 30 sensitive to oil pressure in chamber 28A as described later in connection with FIG. 8.

The system may also incorporate automatic means for limiting the force applied to cable 10. For example, the vertically movable element of the recorder, i.e. the stylus 44, cooperates with a fixed limit switch 100 (FIG. 2) which when actuated by the stylus 44 causes the hydraulic control 70 to stop the hydraulic pump and thereby prevent more than a predetermined force to be applied to cable 10. Alternatively or additively actuation of switch 100 may cause the pressure previously developed in line 74 to be released and pressure to be applied to line 72 to cause the piston 26 to descend.

While for purposes of simplicity in description and illustration only one cable 10 is shown and discussed, it will be appreciated that the invention is applicable also to simultaneous stressing of a multiple number of cables in which case the force on any one or more or all of such cables may be recorded on an individual or group basis.

Further, it will be appreciated that the gripping means 18, 20 and/or 32, 34 may take forms other than as specifically shown and described herein.

Figure 5:
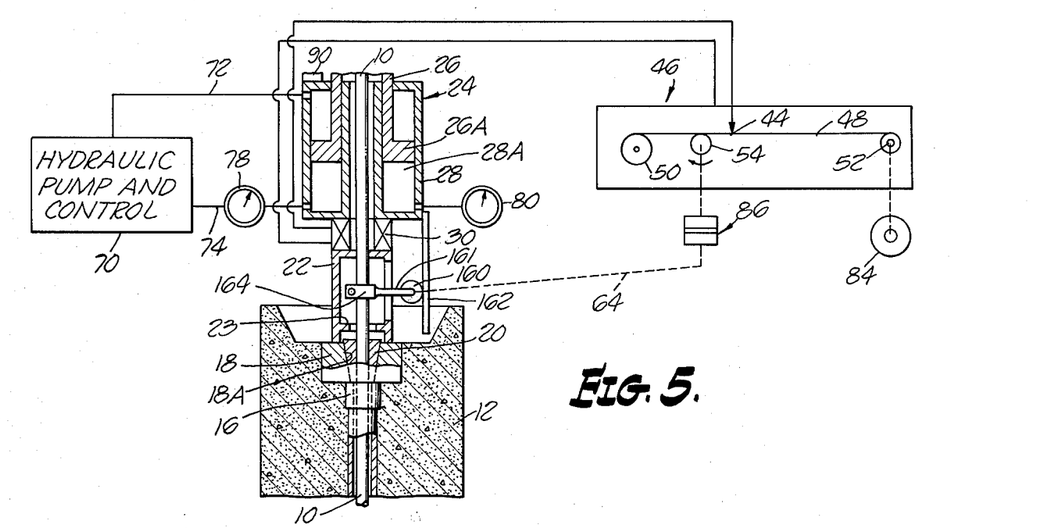
FIG. 5 illustrates a preferred alternate form of the present invention.
Figure 6:
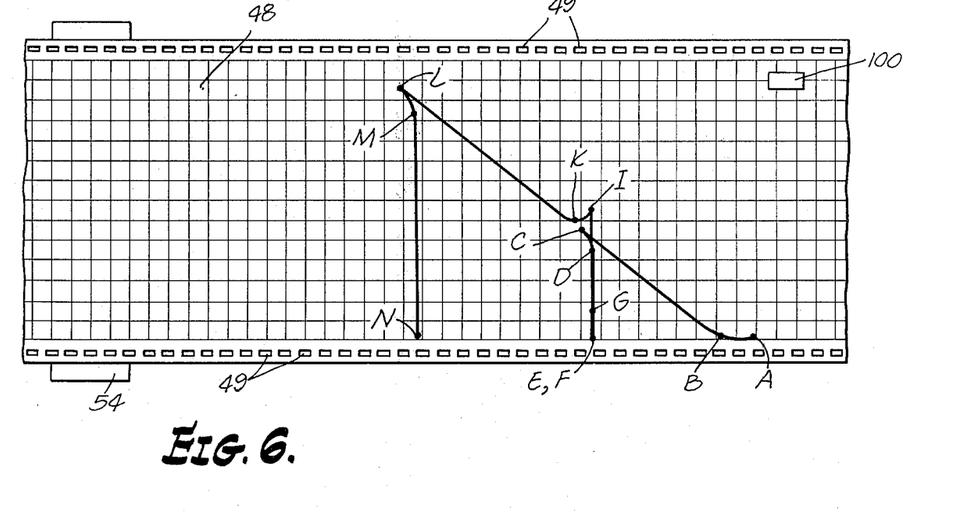
FIG. 6 illustrates the form of recording made in use of the system shown in FIG. 5.

In the form of the invention shown in FIG. 5 the recording media, i.e. paper 48 in FIG. 6 is driven directly in accordance with movement of the cable 10 instead of directly in accordance with movement of piston 26 in FIG. 1 with the advantage that the paper need not be advanced manually or automatically as previously described between successive tensioning operations.

Thus in FIG. 5 the roller 160 (corresponding to roller 60 in FIG. 1) is now mounted on an arm 161 which is clamped by clamp 164 to cable 10, and this roller 160 is guided in track 162 (corresponding to track 62 in FIG. 1) for driving the paper advance roller 54 through connection 64.

Preferably the cable 10 is clamped as close to the anchor 18, 20 as practically possible so as to record the least amount of elongation in that portion of cable 10 above the anchor plate 18 and to provide adequate upward movement. In some cases for repeated number of extensions and contractions clamp 164 is attached to cable 10 above cap 36 (FIG. 1).

In this case the recording shown in FIG. 6 is accomplished when there are two successive tensioning operations and the letters in FIGS. 2 and 6 represent generally the same conditions in these two recordings. In this latter case it will be seen that the lines DE and GE are substantially superimposed because of the lack of necessity of causing the paper to be advanced.

Figures 7, 8:
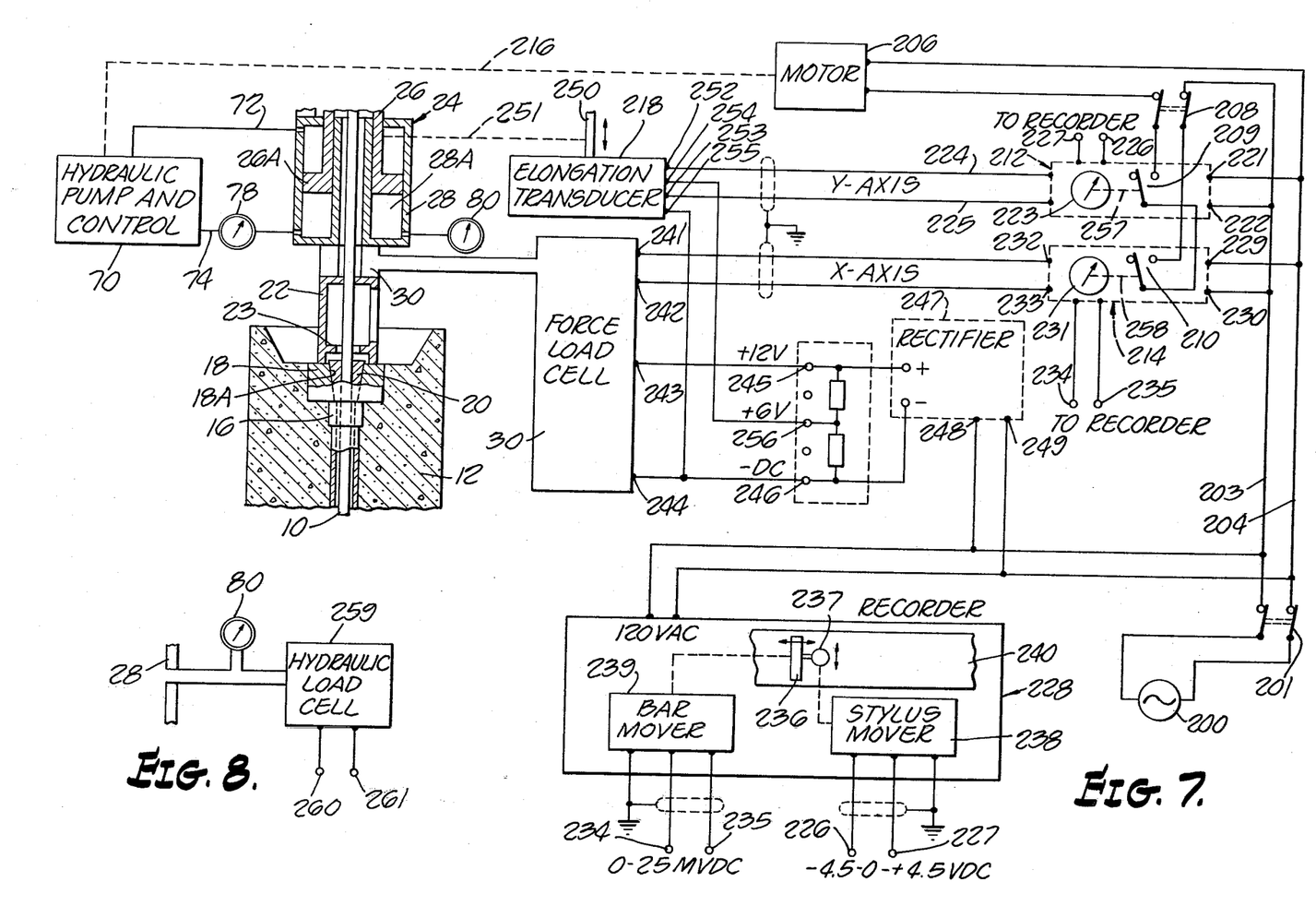
FIG. 7 illustrates a preferred form of the invention particularly useful in commercial operations.
FIG. 8 illustrates another modification which may also be useful in commercial operations.

FIG. 7 illustrates a commercial form of the invention in which the system is fed with power from a conventional A.C. source, 200, through an on-off switch 201.

This voltage appearing on leads 203, 204, is applied to the motor 206 through special switching means which incorporates a plurality of switches indentified as the double-pole-single throw momentary type switch 208 and a pair of single pole-double throw switches 209, 210 in the commercial form of meter units 212, 214. When these switches 208, 209, and 210 are closed, power is applied to the motor 206 which drives the hydraulic pump 70 through a mechanical connection such as a shaft represented by the dottend line 216.

Normally the meter switches 209, 210 are closed and the motor 206 may be energized manually by manual operation of the momentary-type switch 208.

In general, as explained in more detail later, the switch 209 is opened when there is more than a predetermined elongation as established by the output of the elongation transducer 218; and the other switch 210, connected in series with the switch 209 is automatically opened upon attainment of a predetermined force as measured by the load cell 30.

The meter unit 212 is representative of a commercial so-called A.P.I. Relay Meter Model No. 503X which includes a pair of A.C. input terminals 221, 222 for supplying sufficient power to produce a visual indication on meter 223 of the signal derived from the elongation transducer 218, such signal being transferred to the unit 212 via the leads 224, 225. Also the unit 212 is connected via terminals 226, 227 to the recorder unit 228 which as shown in the lower left hand corner of FIG. 7 also includes the same terminals 226, 227.

Likewise the other like meter unit 214 includes a pair of A.C. input terminals, 229, 230 for providing sufficient enrgy to achieve a visual indication on the meter 231 of the signal derived from the force load cell 30, the output of which is applied to the input terminals 232, 233. Also a voltage representative of that signal indicated by meter 231 is supplied via terminals 234, 235 to the previously mentioned recorder unit 228 for achieving a horizontal movement of a stylus-carrying bar 236. The stylus 237 slidably mounted on the bar 236 is moved in a vertical direction by the stylus mover 238 and the bar 236 itself is moved in a horizontal direction by the bar mover 239. The stylus 237 is thus moved in both a vertical and a horizontal direction so as to achieve a recording on the paper 240 which itself remains stationary when the recording is made. The recorder 228 is representative of the type furnished by Hewlett-Packard.

It will be seen that the force load cell 30 is positioned between the hydraulic cylinder 28 and the jack stand 22 as is also the case in the form of the invention illustrated in FIG. 5. Of course, the load cell 30 may be positioned as otherwise described and alluded to herein before. The force load cell 30 may be of the type supplied by Transducer, Inc., which as indicated has four terminals 241, 242, 243, and 244. It is noted that the terminals 241 and 242 are connected respectively to the terminals 232 and 233 of the meter unit 214. The other terminals 243, 244 are connected respectively to the plus 12 volt terminal 245 and the -0- or negative terminal 246 to which a rectified D.C. voltage is applied from a rectified 247 which has its input terminals 248, 249 connected to the previously mentioned power leads 203, 240 respectively.

The elongation transducer 218 is in the form of a transformer and is representative of the type furnished by Hewlett-Packard and in this case it includes a moveable control element 250 which as indicated by the by the dotted line 251 is mechanically connected to the piston 26 so as to achieve an electrical output or electrical condition representative of the position of the piston 26. The transducer 218 has its output terminals 252, 253 connected respectively to the previously mentioned leads 224, 225. The other terminals 254, 255, are connected respectively to the plus 6 volt terminal 256 and the previously mentioned negative terminal 246.

The previously mentioned switches 209, 210 may be manually adjusted so as to operate respectively at a pre-determined elongation and pre-determined force. Thus as illustrated the moveable element of the meters 223, 231 may be mechanically coupled or connected via corresponding mechanical connections 257, 258 (indicated by dotted lines) to the moveable switch arms of corresponding switches 209, 210. To achieve an opening of the corresponding switch when either one of the previously mentioned conditions occurs, i.e., attainment of a predetermined elongation or a pre-determined force, the switches 209, 210 may, for example, be in the form of micro-switches which may be spring-loaded so that they return to their closed positions automatically after the elongation or correspondingly the force returns to a value below the corresponding pre-set value.

As alluded to previously, the load cell 30 may be made responsive to the pressure within the cylinder 28 and this is illustrated in FIG. 8 wherein the hydraulic load cell 259 is then responsive to the pressure with the cylinder 28 and serves to develop an electrical output signal on its output terminals 260, 261, which terminals are then connected to the terminals 232, 233 in FIG. 7. In operation, a two dimensional recording is produced of all significant events and conditions which occur when and as a cable is being stressed from a slack unstressed condition to a condition of high stress and long elongation as the result of a series of stressing steps, each of which involves repeated automatic clamping and unclamping, to the cable 10 in FIG. 1, of a power operated stressing member, such stressing member being a short stroke double acting piston 26 reciprocated to move from a retracted position (near the bottom of its stationing cylinder 28 to an extended position in each of such series of steps. This two dimensional recording is unique, is of the character shown either in FIGS. 2 or 6, and is produced as now described.

Figure 9:
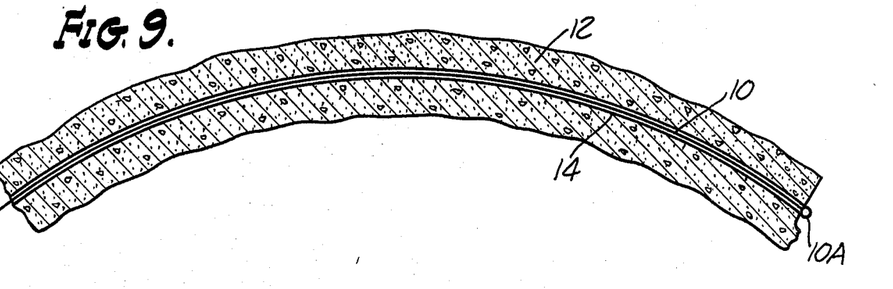
FIG. 9 illustrates in somewhat schematic form conditions under which long lengths of cable are stressed.

In FIGS. 1 and 9 the cable 10 has its end 10A anchored by conventional means (not shown) in concrete 12. A long length of cable 10, which might be from 10 to more than 1000 feet in length, extends slideably through the oversize tube 14 which is curved and is also anchored in concrete 12. Because of the long length of cable 10 which is required to be elongated a distance greater than the stroke of piston 26, the ram 26, 28 is operated through more than one of its cycles of operation. The cable 10 after it emerges from tube 14, extends, in turn through: segments of wedge cable gripping structure 20; the piston-cylinder combination or ram 26, 28; load cell 30; and segments of wedge cable gripping structure 34. The cable gripping structure 34, which is within the piston cap 36 and moves with the piston, is urged by compression spring 40 into clamping engagement with cable 10 so that when piston 26 moves upwardly as a result of hydraulic pressure within cylinder portion 28, the cable portion, so clamped within structure 34 moves upwardly with the piston; and initial slack in the cable between its lower anchored end its upper portion in clamp structure 34 is taken up. After the cable slack is taken up, stress is developed in the cable 10 causing compression of the load cell thereby producing an electrical output, representative of such stress, to the recorder element 14 for producing a recording on paper 48 (FIG. 1 and 2). The paper 48 is moved in accordance with movement of piston 24 using a roller 60 or piston arm 58 mechanically coupled through connections 64 and 86 to the paper drive roll 54. When piston 24 is extended, i.e. moves upwardly, paper 48 moves to the right in FIGS. 1 and 2 and when piston 24 moves downwardly, i.e. is retracted, paper 48 is moved to the left.

Figure 4:
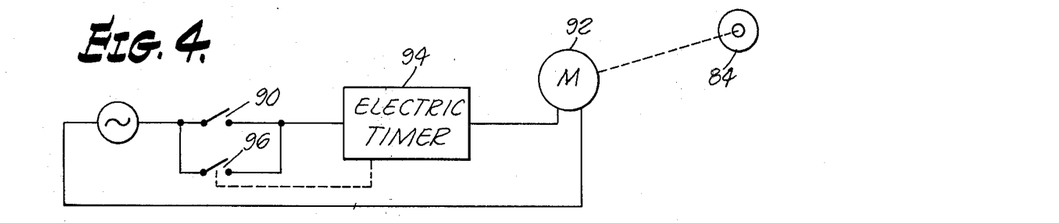
FIG. 4 illustrates features of a recording paper advance useful in the system shown in FIG. 1.

Thus, when as described above, the cable slack is being taken up, that portion A–B of the recording is made. Trace A–B is essentially a straight horizontal line but any forces required to overcome friction or straighten kinks in the cable in tube 14 during the time cable slack is being removed will be revealed by the shape of trace A–B. After all cable slack is removed (point B) further upward movement of piston 26 to the end of its extended travel with the cable still clamped in clamping structure 32 causes the cable to be stressed more and more and this produces the trace B–C. The ordinate of point B is the stress and the horizontal distance between points C and D (shown as $E_1$ in FIG. 2) is the total elongation, i.e. total strain. The slope of trace B–C at any point along such trace B–C is of particular importance and indicative of various conditions as described later. The stress represented by the ordinate of point C is lower than the desired higher stress represented by the ordinate of point M so it becomes necessary to retract piston 26 from its then most extended position to its retracted position from where the piston may again be extended to increase the stress in cable 10. Retraction of piston 10 is caused by applying pressure through line 72 to the upper portion of cylinder 28, and when the piston retracts the cable 10 begins to move downwardly with the piston but such downward movement of the cable 10 causes automatic operation of the wedge segments of one way clamp structure 20 to cause it to clamp the cable thereby preventing further downward movement of the cable i.e. unstressing of the previously stressed cable. The other one way clamp structure 34 automatically releases when and as piston 26 retracts. Conditions prevailing during this transitory condition are represented by the trace C–D with the ordinate of point D being the stress in the cable and the horizontal distance between points B and D being the change in elongation at the time the cable 10 is securely clamped in clamping structure 20. Trace D–C and E–B is representative of conditions during further movement of the piston to its fully retracted position. At this stage, i.e. upon completion of one step in the series of stressing steps, the paper 8 may be moved to the right either manually using the knob 84 or automatically using the modification in FIG. 4 so that in either case the paper is moved preparatory to movement of the piston upwardly. Point F is thus the starting point for the succeeding cycle of events and as the piston begins to move upwardly the clamping structure 34 regrips the cable 10 and this event is characterized by trace F–G. At point G the cable is clamped by structure 34 and further continued upward movement of piston 26 results in stressing of the cable, without producing large elongation, until point H is substantially the same as the ordinate of point D so that further upward movement of piston 26 causes the clamping structure 20 to release and resulting conditions are characterized by trace H–I–K. Conditions which exist during further extended movement of the piston 26 are represented by the character of trace K–L. The ordinate of point L is slightly higher than the desired ultimate lock off stress, which is the ordinate of point M so that such desired stress may be realized after the piston is retracted to cause the clamping structure 20 to again clamp the wire. Conditions which exist during this final clamping and illustrated by trace L–M. Further retractions of piston 20 produces the trace M–N–F.

In the modification shown in FIG. 5 the paper moving roll 54 is directly related to the cable 10 because the arm 161 (FIG. 2) is connected directly to cable 10 instead of using an arm 60 (FIG. 1) connected directly to piston 26 in which case the paper need not be moved (manually or automatically) to the right, as in FIG. 1 and the recording in FIG. 6 is obtained.

In the modification in FIG. 7 the paper remains stationary and means are provided to move the recording stylus not only vertically but also horizontally as well; and in FIG. 8 instead of the force i.e. stress, being monitored by a mechanical load cell, a hydraulic load cell responsive to pressure in the hydraulic cylinder is used.

Figure 10:
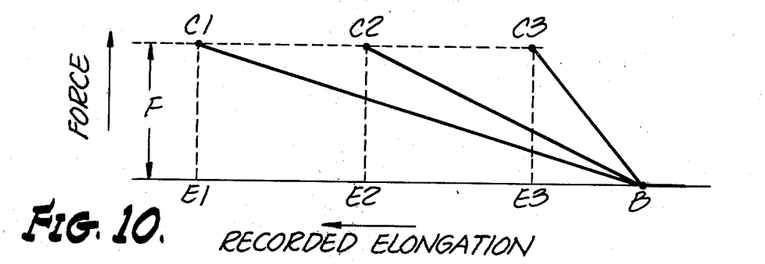
FIGS. 10–12 are graphical illustrations useful in explaining features of the present invention.

As alluded to previously the slope of line BC and also the slope of line KL is revealing of various conditions some of which are now described in relation to FIG. 10.

FIG. 10 shows three lines BC1, BC2, and BC3 each of different slope and being representative respectively of conditions of -no friction-, -low friction-, and -high friction- between the cable 10 and the curved tube 14 (FIG. 9) within which the cable is stressed. Because the tube 14 is curved there will, of course, be frictional forces developed between the cable 10 and tube 14 and these are in accordance with important feature- of the present invention taken into account in establishing the true condition of the cable 10.

It will be seen in FIG. 10 that a particular force represented by the ordinate, F, may result in three different elongations represented by the abscissae BE1, BE2 and BE3. In general it will be seen that the higher the frictional force developed in tube 14 by cable 10, the smaller the elongation and the greater the slope of the line BC (and/or KL) in FIG. 2 or FIG. 3.

The slope of line BC1 (representative of a no friction condition) is an indication of the modulus of elasticity because such slope involves a ratio of stress to strain. Having knowledge of the nominal value of the modulus of elasticity of the cable, which is usually available from the cable manufacturer, some quantitive value of friction, and actual cable stress and actual cable strain may be derived from the recording. Thus the actual cable elongation is not necessarily that elongation which is recorded.

It is further appreciated that while a particular force recorded is not necessarily the same force which exists along the long length of cable 10 within tube 14; and it may be stated generally that under the conditions represented by either line BC2 or BC3 the actual force in the cable decreases in magnitude from the measuring point with the actual force in the cable itself being of smallest value at the cable anchor point 10A.

As indicated above the slope of line BC (and/or KL) in FIGS. 2 and 6 is a measure of the frictional coefficient between the cable 10 and tube 14. After the frictional coefficient is determined (with the aid of known values of modulus of elasticity of the cable itself) one can determine with accuracy the actual stress in the cable at any particular point along its length. Thus important new and improved results are obtained in accordance with feature of the present invention wherein friction is being measured simultaneously with a recorded force and a recorded elongation.

Of major importance is, not an indicated force outside of tube 14 but, knowledge of the actual force in the cable 10 in the tube 14 in relation to the minimum ultimate strength (M.U.S.) of the cable. Usually a limiting stress of 0.75 M.U.S. is achieved and permissive. By the taking into account friction, stressing at 0.75 M.U.S. instead of an erroneous lower stress may be achieved.

Figure 11:
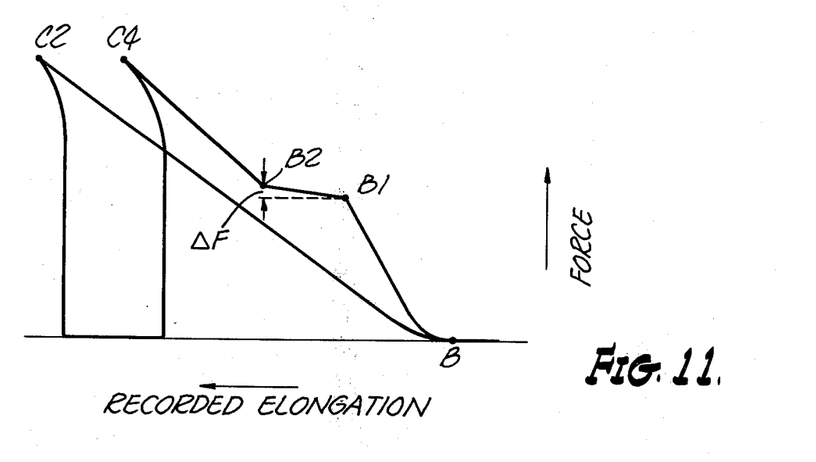

Apart from the slope of recording BC (or KL) abrupt changes in such slope are revealing as to other conditions which prevail or may have prevailed. For example, in FIG. 11 the recording BC2 corresponds to the recording BC2 in FIG. 10 and the recording B, B1, B2, C4 is representative of a condition wherein the cable 10 was temporarily "frozen" in tube 14 and only a relatively small change in recorded force ΔF, was required to produce a very large change in recorded elongation represented by the abscissae B1, B2.

Figure 12:
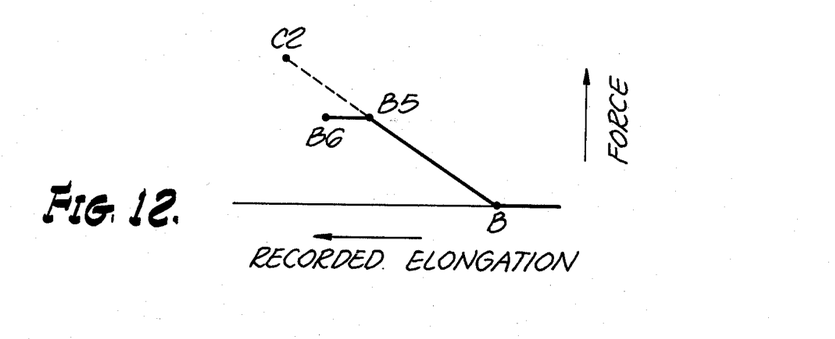

Also any undesired deviation is quality of steel may be detected. For example, in FIG. 12 a recording B, B5, B6 instead of a straight line recording BC2 is indicative of one using an incorrect steel cable such as, for example, through mistake in being supplied with a low strength steel instead of a higher strength steel. When this condition represented in FIG. 12 occurs the elongation represented by the abscissae B, B6 causes operation of the safety means 100 in FIGS. 2 and 6 causing disablement of the ramcylinder 24, 26 as previously described, thereby preventing actual breakage of the steel cable. This is very important since otherwise breakage of a cable under stress can produce great bodily harm to persons in the vicinity.

I claim:

1. A system for prestressing a cable and continuously sensing and recording the force applied to, the axial movement of, and the elongation of the cable comprising:

a first means for releasably engaging the cable, a power operated member operatively associated with said means for engaging the cable such that said member is capable of exerting prestressing force on the cable, recording means having a recording element and a first and second control element which determine the character of the recording made by the recording element, said member being capable of moving said cable in an axial direction and of elongating said cable, a second means for releasably engaging said cable and for preventing substantial loss of the tensile stress applied to the cable by the member when said first means for engaging said cable is disengaged, means for sensing axial movement and elongation of the cable operatively connected to said first control element, means for sensing the force applied to said cable by said member operatively connected to said second control element, said control elements being capable of controlling said recording element in response to said sensing means to produce a simultaneous and continuous record in said recording means of the axial movement of, elongation of, and force applied to the cable.

2. The system of claim 1 wherein said means for sensing axial movement is operatively connected to said power operated member.

3. The system of claim 2 wherein said means for sensing axial movement is a transducer.

4. The system of claim 1 wherein said means for sensing axial movement is operatively connected to said cable.

5. The system of claim 4 wherein said means for sensing axial movement is a transducer.

6. The system of claim 1 wherein said means for sensing force is a load cell.

7. The system of claim 1 wherein said means for sensing force is a force transducer.

8. The system of claim 1 wherein said means for sensing axial movement is an elongation transducer and said means for sensing force is a load cell.

9. The system of claim 1 wherein said power operated member is a piston in a cylinder and is operated by hydraulic power.

10. The system of claim 9 wherein said means for sensing force is responsive to the pressure in said cylinder.

11. The system of claim 10 wherein said means for sensing force is a force transducer.

12. The system of claim 1 including means for disabling said power operated means when the force exerted by said member on said cable exceeds a predetermined value.

13. The system of claim 1 including means for disabling said power operated means when the elongation in the cable exceeds a predetermined value.

14. The system of claim 1 including means for disabling said power operated means when the power operated means moves more than a predetermined distance.

15. The system of claim 1 wherein said first and second means for engaging the cable are wedge clamps.

16. The system of claim 1 wherein said recording means includes a medium upon which a recording is made, which medium is moved in response to said means for sensing axial movement.

17. The system of claim 1 wherein said means for sensing force is operatively connected to an element for controlling the power supplied to said power operated member.

18. A system for prestressing a cable and continuously sensing and recording the force applied to, the axial movement of, and the elongation of the cable comprising:
a first means for releasably engaging the cable,
a power operated member operatively associated with said means for engaging the cable such that said member is capable of exerting prestressing force on the cable,
recording means having a recording element and a first and second control element which determine the character of the recording made by the recording element,
said member being capable of moving said cable in an axial direction and of elongating said cable,
a second means for releasably engaging said cable and for preventing substantial loss of the tensile stress applied to the cable by the member when said first means for engaging said cable is disengaged,
means for sensing axial movement and elongation of the cable operatively connected to said first control element,
means for sensing the force applied to said cable by said member operatively connected to said second control element,
said control elements being capable of controlling said recording element in response to said sensing means to produce a simultaneous and continuous record in said recording means of the axial movement of, elongation of, and force applied to the cable,
wherein the means for sensing force is located between said power operated member and said first means for engaging the cable.

19. A system for prestressing a cable and continuously sensing and recording the force applied to, the axial movement of, and the elongation of the cable comprising:
a first means for releasably engaging the cable,
a power operated member operatively associated with said means for engaging the cable such that said member is capable of exerting prestressing force on the cable,
recording means having a recording element and a first and second control element which determine the character of the recording made by the recording element,
said member being capable of moving said cable in an axial direction and of elongating said cable,
a second means for releasably engaging said cable and for preventing substantial loss of the tensile stress applied to the cable by the member when said first means for engaging said cable is disengaged,
means for sensing axial movement and elongation of the cable operatively connected to said first control element,
means for sensing the force applied to said cable by said member operatively connected to said second control element,
said control elements being capable of controlling said recording element in response to said sensing means to produce a simultaneous and continuous record in said recording means of the axial movement of, elongation of, and force applied to the cable,
wherein said means for sensing force is located between said power operated member and said first means for engaging the cable.

20. A system for prestressing a cable and continuously sensing and recording the force applied to, the axial movement of, and the elongation of the cable comprising:
a first means for releasably engaging the cable,
a power operated member operatively associated with said means for engaging the cable such that said member is capable of exerting prestressing force on the cable,
recording means having a recording element and a first and second control element which determine the character of the recording made by the recording element,
said member being capable of moving said cable in an axial direction and of elongating said cable,
a second means for releasably engaging said cable and for preventing substantial loss of the tensile stress applied to the cable by the member when said first means for engaging said cable is disengaged, means for sensing axial movement and elongation of the cable operatively connected to said first control element, means for sensing the force applied to said cable by said member operatively connected to said second control element, said control elements being capable of controlling said recording element in response to said sensing means to produce a simultaneous and continuous record in said recording means of the axial movement of, elongation of, and force applied to the cable, wherein said power operated member is a piston movable in a cylinder and a stationary jack stand is provided for said cylinder, said means for sensing force being positioned between said jack stand and said cylinder.

21. A system for prestressing a cable and continuously sensing and recording the force applied to, the axial movement of, and the elongation of the cable comprising a first clamping means for releasably clamping the cable, a power operated member operatively associated with said first clamping means such that said member is capable of exerting prestressing force on the cable, recording means having a recording element and a first and second control element which determine the character of the recording made by the recording element, said member being capable of moving said cable in an axial direction and of elongating said cable, a second clamping means for releasably engaging said cable and for preventing substantial loss of the tensile stress applied to the cable by the member when said first clamping means is disengaged, an elongation transducer for sensing axial movement and elongation of the cable operatively connected to said first control element, a load cell for sensing the force applied to said cable by said member operatively connected to said second control element, said control elements being capable of controlling said recording element in response to said sensing means to produce a simultaneous and continuous record in said recording means of the axial movement of, elongation of, and force applied to the cable.

* * * * *